US011633577B2

(12) United States Patent
Nitzan et al.

(10) Patent No.: US 11,633,577 B2
(45) Date of Patent: Apr. 25, 2023

(54) SYSTEMS AND METHODS FOR TREATING PULMONARY EDEMA

(71) Applicant: White Swell Medical Ltd, Kibbutz Shefayim (IL)

(72) Inventors: Yaacov Nitzan, Hertzelia (IL); Menashe Yacoby, Ramat Gan (IL); Tanhum Feld, Merhavya (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 434 days.

(21) Appl. No.: 16/197,667

(22) Filed: Nov. 21, 2018

(65) Prior Publication Data

US 2019/0083761 A1    Mar. 21, 2019

Related U.S. Application Data

(63) Continuation of application No. 14/726,715, filed on Jun. 1, 2015, now Pat. No. 10,300,254.
(Continued)

(51) Int. Cl.
*A61M 1/36* (2006.01)
*A61M 27/00* (2006.01)
(Continued)

(52) U.S. Cl.
CPC ............ *A61M 27/002* (2013.01); *A61M 1/34* (2013.01); *A61M 1/3639* (2013.01);
(Continued)

(58) Field of Classification Search
CPC .... A61M 1/34; A61M 1/3639; A61M 1/3653; A61M 1/3655; A61M 1/3659;
(Continued)

(56) References Cited

U.S. PATENT DOCUMENTS 3,211,150 A    10/1965   Foderick
3,884,240 A    5/1975   Gilman
(Continued)

FOREIGN PATENT DOCUMENTS

EP    0526102 A1    2/1993
EP    2353501 A1    8/2011
(Continued)

OTHER PUBLICATIONS

International Search Report and Written Opinion dated Oct. 30, 2018, for PCT/IB18/000364, filed Mar. 19, 2018 (9 pages).
(Continued)

*Primary Examiner* — Kai H Weng
(74) *Attorney, Agent, or Firm* — Brown Rudnick LLP; Adam M. Schoen

(57) ABSTRACT

Various systems and methods are provided for treating pulmonary edema. In general, a pump can be configured to be implanted within a patient at risk of developing edema. The pump can be configured to pump fluid out of the patient's lungs, e.g., out of the patient's interstitial and alveolar spaces. The pump can be configured to be fully implanted within the patient's body. The pump can be configured to continuously pump fluid, or the pump can be configured to be selectively actuatable in response to a trigger event. In an exemplary embodiment, the pump can include an inflow port coupled to an inflow tube in fluid communication with a lymphatic vessel of the patient, and can include an outflow port coupled to an outflow tube in fluid communication with a vein of the patient.

17 Claims, 8 Drawing Sheets

Related U.S. Application Data

(60) Provisional application No. 62/006,206, filed on Jun. 1, 2014.

(51) Int. Cl.
  *A61M 1/34* (2006.01)
  *A61M 25/00* (2006.01)
  *A61M 25/10* (2013.01)

(52) U.S. Cl.
  CPC ........ *A61M 1/3653* (2013.01); *A61M 1/3655* (2013.01); *A61M 1/3659* (2014.02); *A61M 25/0026* (2013.01); *A61M 25/1011* (2013.01); *A61M 2025/0002* (2013.01); *A61M 2025/1015* (2013.01); *A61M 2025/1052* (2013.01); *A61M 2202/0405* (2013.01); *A61M 2205/10* (2013.01); *A61M 2205/3331* (2013.01); *A61M 2205/3334* (2013.01)

(58) Field of Classification Search
  CPC .. A61M 2025/0002; A61M 2025/1015; A61M 2025/1052; A61M 2202/0405; A61M 2205/10; A61M 2205/3331; A61M 2205/3334; A61M 25/0026; A61M 25/1011; A61M 27/002
  See application file for complete search history.

(56) References Cited

U.S. PATENT DOCUMENTS

| | | |
|---|---|---|
| 3,926,175 A | 12/1975 | Allen et al. |
| 4,714,460 A | 12/1987 | Calderon |
| 4,822,341 A | 4/1989 | CoIone |
| 4,838,864 A | 6/1989 | Peterson |
| 4,957,484 A | 9/1990 | Murtfeldt |
| 5,005,564 A | 4/1991 | Grundei et al. |
| 5,069,662 A | 12/1991 | Bodden |
| 5,092,844 A | 3/1992 | Schwartz et al. |
| 5,097,840 A | 3/1992 | Wallace et al. |
| 5,366,504 A | 11/1994 | Andersen et al. |
| 5,391,143 A | 2/1995 | Kensey |
| 5,484,412 A | 1/1996 | Pierpont |
| 5,509,897 A | 4/1996 | Twardowski et al. |
| 5,554,119 A | 9/1996 | Harrison et al. |
| 5,558,642 A | 9/1996 | Schweich, Jr. et al. |
| 5,702,364 A | 12/1997 | Euteneuer |
| 5,716,340 A | 2/1998 | Schweich, Jr. et al. |
| 5,817,046 A | 10/1998 | Glickman |
| 5,836,912 A | 11/1998 | Kusleika |
| 5,893,841 A | 4/1999 | Glickman |
| 5,897,533 A | 4/1999 | Glickman |
| 5,908,407 A | 6/1999 | Frazee et al. |
| 5,919,163 A * | 7/1999 | Glickman ........... A61M 1/3615 604/101.05 |
| 5,921,913 A | 7/1999 | Siess |
| 6,042,569 A | 3/2000 | Finch, Jr. et al. |
| 6,139,517 A | 10/2000 | Macoviak et al. |
| 6,152,945 A | 11/2000 | Bachinski et al. |
| 6,165,196 A | 12/2000 | Stack et al. |
| 6,179,796 B1 | 1/2001 | Waldridge |
| 6,183,492 B1 | 2/2001 | Hart et al. |
| 6,248,091 B1 | 6/2001 | Voelker |
| 6,254,563 B1 | 7/2001 | Macoviak et al. |
| 6,443,884 B1 * | 9/2002 | Miyawaki ........... A61M 60/554 623/3.28 |
| 6,503,224 B1 | 1/2003 | Forman et al. |
| 6,524,323 B1 | 2/2003 | Nash et al. |
| 6,555,057 B1 | 4/2003 | Bendera |
| 6,616,623 B1 * | 9/2003 | Kutushov ............. A61M 1/36 210/695 |
| 6,635,068 B1 | 10/2003 | Dubrul et al. |
| 6,699,231 B1 | 3/2004 | Sterman et al. |
| 6,878,140 B2 | 4/2005 | Barbut |
| 6,936,057 B1 | 8/2005 | Nobles |
| 7,022,097 B2 | 4/2006 | Glickman |
| 7,195,608 B2 | 3/2007 | Burnett |
| 7,645,259 B2 | 1/2010 | Goldman |
| 7,766,892 B2 | 8/2010 | Keren et al. |
| 7,780,628 B1 | 8/2010 | Keren et al. |
| 8,109,880 B1 | 2/2012 | Pranevicius et al. |
| 8,126,538 B2 | 2/2012 | Shuros et al. |
| 8,216,122 B2 | 7/2012 | Kung |
| 8,480,555 B2 | 7/2013 | Kung |
| 8,679,057 B2 | 3/2014 | Fulton, III et al. |
| 9,179,921 B1 | 11/2015 | Morris |
| 9,405,942 B2 | 8/2016 | Liao et al. |
| 9,421,316 B2 | 8/2016 | Leeflang et al. |
| 9,433,713 B2 | 9/2016 | Corbett et al. |
| 9,486,566 B2 | 11/2016 | Siess |
| 9,533,054 B2 | 1/2017 | Yan et al. |
| 9,533,084 B2 | 1/2017 | Siess et al. |
| 9,642,991 B2 | 5/2017 | Eversull et al. |
| 9,669,142 B2 | 6/2017 | Spanier et al. |
| 9,669,144 B2 | 6/2017 | Spanier et al. |
| 9,675,739 B2 | 6/2017 | Tanner et al. |
| 9,682,223 B2 | 6/2017 | Callaghan et al. |
| 9,750,861 B2 | 9/2017 | Hastie et al. |
| 9,770,543 B2 | 9/2017 | Tanner et al. |
| 9,878,080 B2 | 1/2018 | Kaiser et al. |
| 9,901,722 B2 | 2/2018 | Nitzan et al. |
| 9,962,170 B2 | 5/2018 | Jansen et al. |
| 10,149,684 B2 | 12/2018 | Nitzan et al. |
| 10,154,846 B2 | 12/2018 | Nitzan et al. |
| 10,195,405 B2 | 2/2019 | Nitzan et al. |
| 10,207,086 B2 | 2/2019 | Nitzan et al. |
| 10,226,604 B2 | 3/2019 | Nitzan et al. |
| 10,226,605 B2 | 3/2019 | Nitzan et al. |
| 10,245,363 B1 | 4/2019 | Rowe |
| 10,285,708 B2 | 5/2019 | Nitzan et al. |
| 10,300,254 B2 | 5/2019 | Nitzan et al. |
| 10,639,460 B2 | 5/2020 | Nitzan et al. |
| 10,653,871 B2 | 5/2020 | Nitzan et al. |
| 10,709,878 B2 | 7/2020 | Nitzan et al. |
| 10,912,873 B2 | 2/2021 | Nitzan et al. |
| 10,926,069 B2 | 2/2021 | Nitzan et al. |
| 10,960,189 B2 | 3/2021 | Nitzan et al. |
| 11,007,353 B2 | 5/2021 | Gerrans et al. |
| 11,166,730 B2 | 11/2021 | Nitzan et al. |
| 11,179,550 B2 | 11/2021 | Nitzan et al. |
| 11,179,551 B2 | 11/2021 | Nitzan et al. |
| 11,179,552 B2 | 11/2021 | Nitzan et al. |
| 11,357,959 B2 | 6/2022 | Nitzan et al. |
| 11,406,393 B2 | 8/2022 | Nitzan |
| 2002/0010418 A1 | 1/2002 | Lary et al. |
| 2003/0093109 A1 | 5/2003 | Mauch |
| 2003/0134416 A1 | 7/2003 | Yamanishi et al. |
| 2003/0208097 A1 | 11/2003 | Aboul-Hosn et al. |
| 2004/0006306 A1 | 1/2004 | Evans et al. |
| 2004/0064091 A1 | 4/2004 | Keren et al. |
| 2004/0147871 A1 | 7/2004 | Burnett |
| 2004/0210296 A1 | 10/2004 | Schmitt et al. |
| 2004/0230181 A1 | 11/2004 | Cawood |
| 2005/0228474 A1 | 10/2005 | Laguna |
| 2005/0251180 A1 | 11/2005 | Burton et al. |
| 2006/0030814 A1 | 2/2006 | Valencia et al. |
| 2006/0064059 A1 | 3/2006 | Gelfand et al. |
| 2006/0100658 A1 | 5/2006 | Obana et al. |
| 2006/0161095 A1 | 7/2006 | Aboul-Hosn et al. |
| 2006/0178604 A1 | 8/2006 | Alderman |
| 2007/0055299 A1 | 3/2007 | Ishimaru et al. |
| 2007/0282303 A1 | 12/2007 | Nash et al. |
| 2007/0282382 A1 | 12/2007 | Shuros et al. |
| 2008/0009719 A1 | 1/2008 | Shuros et al. |
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0168649 A1 | 7/2010 | Schwartz et al. |

(56) References Cited

U.S. PATENT DOCUMENTS

| | | |
|---|---|---|
| 2010/0179389 A1 | 7/2010 | Moroney, III et al. |
| 2010/0280451 A1 | 11/2010 | Teeslink et al. |
| 2010/0318114 A1 | 12/2010 | Pranevicius et al. |
| 2011/0004046 A1 | 1/2011 | Campbell et al. |
| 2011/0092955 A1 | 4/2011 | Purdy et al. |
| 2011/0257462 A1 | 10/2011 | Rodefeld et al. |
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 | 2/2012 | Callaghan et al. |
| 2012/0157913 A1 | 6/2012 | Aziz et al. |
| 2012/0178986 A1 | 7/2012 | Campbell et al. |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0177432 A1 | 7/2013 | Toellner et al. |
| 2013/0237954 A1 | 9/2013 | Shuros et al. |
| 2013/0245607 A1 | 9/2013 | Eversull et al. |
| 2013/0303969 A1 | 11/2013 | Keenan et al. |
| 2013/0317535 A1 | 11/2013 | Demmy |
| 2013/0331814 A1 | 12/2013 | Fulton, III et al. |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1* | 10/2014 | Franano ............ A61M 1/3659 600/17 |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0166463 A1 | 6/2016 | Douglas et al. |
| 2016/0169630 A1 | 6/2016 | Augustine et al. |
| 2016/0213826 A1 | 7/2016 | Tanner et al. |
| 2016/0331378 A1 | 11/2016 | Nitzan et al. |
| 2017/0014563 A1 | 1/2017 | Khir |
| 2017/0095395 A1 | 4/2017 | Wennen et al. |
| 2017/0197021 A1 | 7/2017 | Nitzan et al. |
| 2017/0224512 A1 | 8/2017 | Hingston |
| 2017/0319764 A1 | 11/2017 | Tanner et al. |
| 2018/0012630 A1 | 1/2018 | Thomee et al. |
| 2018/0020456 A1 | 1/2018 | Wan et al. |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2018/0303986 A1 | 10/2018 | Meacham |
| 2019/0014991 A1 | 1/2019 | Maki et al. |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0030586 A1 | 1/2020 | Nitzan et al. |
| 2020/0030587 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0261706 A1 | 8/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0121678 A1 | 4/2021 | Nitzan et al. |
| 2021/0378676 A1 | 12/2021 | Keating et al. |
| 2021/0378677 A1 | 12/2021 | Keating et al. |
| 2021/0378678 A1 | 12/2021 | Keating et al. |
| 2021/0379329 A1 | 12/2021 | Keating et al. |
| 2022/0039803 A1 | 2/2022 | Nitzan et al. |
| 2022/0104827 A1 | 4/2022 | Keating et al. |
| 2022/0104828 A1 | 4/2022 | Keating et al. |
| 2022/0218360 A1 | 7/2022 | Nitzan et al. |
| 2022/0218961 A1 | 7/2022 | Nitzan et al. |
| 2022/0280761 A1 | 9/2022 | Nitzan et al. |
| 2022/0280762 A1 | 9/2022 | Nitzan et al. |
| 2022/0331510 A1 | 10/2022 | Amstutz et al. |

FOREIGN PATENT DOCUMENTS

| | | |
|---|---|---|
| EP | 2353503 A1 | 8/2011 |
| EP | 2353632 A1 | 8/2011 |
| EP | 2497524 A1 | 9/2012 |
| EP | 2637927 A1 | 9/2013 |
| WO | 89/04193 A1 | 5/1989 |
| WO | 2000/024337 A2 | 5/2000 |
| WO | 01/013983 A2 | 3/2001 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2018/158636 A1 | 9/2018 |
| WO | 2018172848 A2 | 9/2018 |
| WO | 2018/202776 A1 | 11/2018 |
| WO | 2019/027380 A1 | 2/2019 |
| WO | 2020/174285 A2 | 9/2020 |

OTHER PUBLICATIONS

International Search Report and Written Opinion dated Jun. 25, 2018, for PCT/IB18/00263, filed Mar. 1, 2018 (10 pages).
International Search Report and Written Opinion dated Apr. 12, 2018, for PCT/IB17/01488, filed Oct. 31, 2017 (11 pages).
Non-Final Rejection issued in U.S. Appl. No. 16/867,047, dated Sep. 16, 2020, 11 pages.
Non-Final Office Action issued in U.S. Appl. No. 15/799,562, dated Jul. 28, 2020 (8 pages).
Non-Final Office Action issued in U.S. Appl. No. 15/870,111, dated Jun. 24, 2020 (5 pages).
Bannon, 2011, Anatomic considerations for central venous cannulation, Risk Manag Healthc Policy 4:27-39.
Moscucci, 2014, Section III Hemodynamic principles 10 Pressure measurement, 223-244 in Grossman & Bairn's Cardiac Catheterization, Angiography, and Intervention 8 Ed.
Shimizu, 2014, Embolization of a fractured central venous catheter placed using the internal jugular apporach, Int J Surg Case Rep 5:219.
Stone, 2010, The effect of rigid cervical collars on internal jugular vein dimensions, Acad Emerg Med 17(1): 100-102.
Swan, 1970, Catheterization of the Heart in Man with Use of a Flow-directed Balloon-tipped Catheter, NEJM 283(9):447-451.
Yancy, 2013, 2013 ACCF/AHA Guideline for the Management of Heart Failure, Circulation 128(16):e240-e327.

(56) References Cited

OTHER PUBLICATIONS

Biran, 2017, Heparin coatings for improving blood compatibility of medical devices, Adv Drug Delivery Rev, 112:12-23.
Webb, 2012, Roughness parameters for standard description of surface nanoarchitecture, Scanning 34:257-263.
Blitz, 2014, Pump thrombosis—a riddle wrapped in a mystery inside an enigma, Ann Cardiothorac Surg, 3(5):450-471.
Chikly, 2005, Manual techniques addressing the lymphatic system: origins and development, JAOA 105(10):457-464.
Ratnayake, 2018, The Anatomy and physiology of the terminal thoracic duct and ostial valve in health and disease: potential implications for intervention, J Anat 233:1-14.
Tchantchaleishvili, 2014, Evaluation and treatment of pump thrombosis and hemolysis, Ann Cardiothorac Surg, 3(5):490-495.

* cited by examiner

SYSTEMS AND METHODS FOR TREATING PULMONARY EDEMA

CROSS REFERENCE

The present application is a continuation of U.S. nonprovisional application Ser. No. 14/726,715, filed Jun. 1, 2015, which claims priority to U.S. Provisional Patent Application No. 62/006,206 entitled "System And Method For Treatment of Pulmonary Edema" filed Jun. 1, 2014, the content of each of which is hereby incorporated by reference in its entirety.

FIELD

The present disclosure relates generally to systems and methods for treating pulmonary edema.

BACKGROUND

The lymphatic system is part of the circulatory system in conjunction with the arterial and venous systems. A primary function of the lymphatic system is to drain excessive interstitial fluid back into the venous system at two main locations: the thoracic duct and the lymphatic duct, which drain into the left and right subclavian veins, respectively.

Under normal circulatory conditions of the arterial and venous systems the interstitial fluid volume balance is maintained and the lymph fluid is cleared back through the lymphatic system. In pathological conditions such as Acute Cardiogenic Pulmonary Edema and chronic heart failure, the capillary hydrostatic pressure and the venous pulmonary pressure can become elevated and fluid flows excessively out of the blood vessels and into the interstitial and alveolar spaces. The pressure gradient between the initial lymphatics and at the outflow of the thoracic duct and the lymphatic duct is reduced and the lymphatic system cannot clear the additional fluid which accumulates in the air spaces of the lungs. This is a life threatening condition as gas exchange is impaired to the extent that it may lead to respiratory failure.

Current treatment methods require extended hospitalization and treatment with loop diuretics and/or vasodilators. Oftentimes patients must also receive supplemental oxygen or, in more extreme cases, require mechanical ventilation. Many of these treatment methods are less than ideal because the edema is not always alleviated rapidly enough and for many patients renal function is adversely affected. A significant percentage of patients do not respond to this treatment and a significant percentage must be readmitted to a hospital within 30 days.

A significant problem with current treatment protocol is that it is based on the need to reduce intravascular blood pressure to move lymphatic fluid back into the vasculature. The reduction of intravascular blood pressure leads to leads to hypotension and activates the Renin Angiotenesin Aldesterone System, which leads to an increase in blood pressure. Eventually, this cycle leads to diuretic resistance and the worsening of renal function in almost 30% of admitted patients.

Accordingly, there remains a need for improved methods and devices for systems and methods for treating pulmonary edema.

SUMMARY

Various systems and methods are provided for treating pulmonary edema. In one embodiment a system for treatment of edema includes a pump configured to be implanted in a body of a patient, an inflow tube fluidically coupled to an inflow port of the pump and configured to be implanted into the body of the patient so as to bring the inflow port into fluid communication with a lymphatic vessel of the patient, and an outflow tube fluidically coupled to an outflow port of the pump and configured to be implanted into the body of the patient so as to bring the outflow port into fluid communication with a vein in the body of the patient such that the pump is operative to pump fluid from the lymphatic vessel to the vein.

The system can vary in any number of ways. For example, the system can include a controller configured to actuate the pump. The controller can be configured to actuate the pump in response to user operation of a control external to the body of the patient, and/or the system can include a pressure sensor configured to be implanted in the body of the patient. The controller can be configured to actuate the pump in response to a pressure measured by the pressure sensor exceeding a predefined threshold, and/or the controller can be configured to control a speed of operation of the pump depending on a pressure measured by the pressure sensor.

For another example, the pump can be configured to continuously pump the fluid from the lymphatic vessel to the vein.

For yet another example, the system can include a power source configured to be implanted in the body of the patient and configured to provide power to the pump.

For another example, the system can include a charging coil configured to inductively couple to a power source external to the body of the patient and thereby provide power to the pump.

For yet another example, the pump can be configured to pump fluid at a rate in a range of about 10 to 1000 ml/hour, e.g., in a range of about 10 to 200 ml/hour.

In another aspect, a method is provided that in one embodiment includes implanting a pump in a body of a patient, the pump being operable to convey a bodily fluid from an inflow port of the pump to an outflow port of the pump, arranging a first tube in fluid communication with the inflow port to be in fluid communication with a lymphatic vessel of the patient, and arranging a second tube in fluid communication with the outflow port to be in fluid communication with a vein of the patient such that the pump is operable to convey fluid from the lymphatic vessel to the vein.

The method can have any number of variations. For example, the method can include actuating the pump, thereby causing the pump to convey the fluid, e.g., lymph, from the lymphatic vessel to the vein of the patient. The actuated pump can maintain an outflow pressure in a range of about 2 to 6 mmHg, the pump can be actuated in response to user operation of a control external to the body of the patient, and/or the pump can be configured to be actuated periodically or continuously.

For another example, the lymphatic vessel can include one of a thoracic duct of the patient and a lymphatic duct of the patient.

For yet another example, the vein can include one of the patient's subclavian vein, internal jugular vein, innominate vein, and superior vena cava.

For still another example, the method can include implanting a pressure sensor in a location within the body of the patient that enables the pressure sensor to measure pressure in a desired region of the body of the patient. The method can include measuring the pressure in the desired region using the pressure sensor, and actuating the pump in response to the measured pressure exceeding a predefined threshold and/or controlling a speed of operation of the pump depending on the measured pressure.

For another example, the pump can be implanted adjacent to one of a junction of the patient's left subclavian vein and internal jugular vein and a junction of the patient's right subclavian vein and internal jugular vein.

For yet another example, the pump can include a power source, and the method can include recharging the power source by inductive coupling to a power source external to the body of the patient.

For another example, the pump can include a power source, and the method can include recharging the power source by inductive coupling to a power source external to the body of the patient.

For still another example, the method can include advancing a wire into the body of the patient and into the lymphatic vessel, verifying the position of the wire within the lymphatic vessel, and then arranging the first tube.

BRIEF DESCRIPTION OF DRAWINGS

This invention will be more fully understood from the following detailed description taken in conjunction with the accompanying drawings, in which.

DETAILED DESCRIPTION

Figure 1:
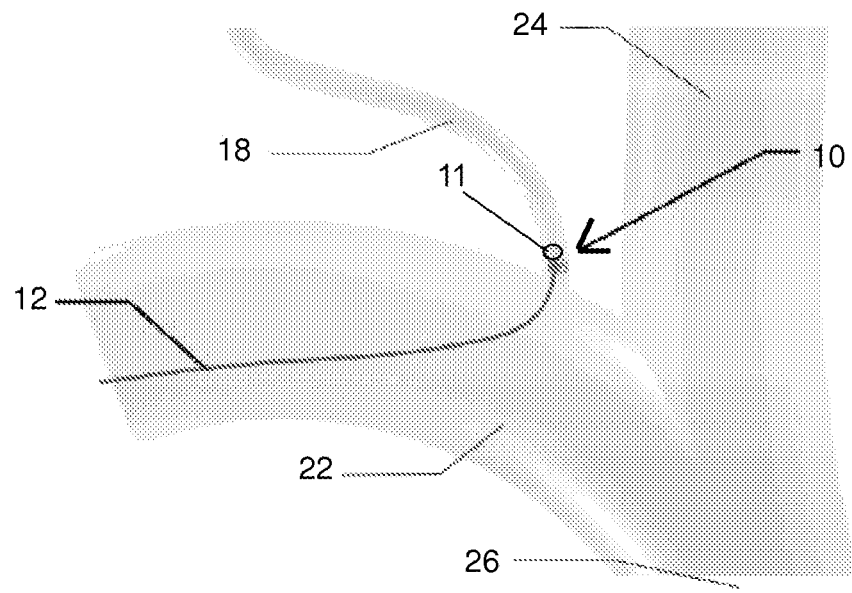
FIG. 1 is a perspective view of an embodiment of an implantable pump implanted in a body.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various systems and methods are provided for treating pulmonary edema. In general, a pump can be configured to be implanted within a patient at risk of developing edema. The pump can be configured to pump fluid out of the patient's lungs, e.g., out of the patient's interstitial and alveolar spaces, which can help prevent the fluid from building up to a dangerous degree. The pump can thus be configured to facilitate prevention of edema by limiting fluid build-up in the lungs, if not preventing fluid build-up entirely. In other words, the pump can be configured to facilitate treatment of chronic edema, such as can occur in connection with chronic heart failure. The pump can be configured to facilitate higher lymphatic return by lowering outflow pressure at a lymphatic vessel of the patient, e.g., at the patient's thoracic duct and/or lymphatic duct. The pump can be configured to be fully implanted within the patient's body, thereby helping the device to be unobtrusive in the patient's daily life, similar to a pacemaker. The pump can be configured to continuously pump fluid, which can help ensure the removal of fluid that collects in the lung space before a dangerous amount of the fluid builds up and/or can help ensure the long term patency of the pump. In other words, the pump can be configured to continuously run and provide fluid flow. Alternatively, the pump can be configured to be selectively actuatable in response to a trigger event, such as in response to a value of a measured parameter (e.g., pressure, fluid amount, bioimpedance, heart rate, breathing rate, patient activity level, organ dimension, etc.) or in response to a user input requesting pumping. The pump can thus be configured to only periodically pump fluid, e.g., only periodically run so as to alternate between periods in which the pump is running to provide fluid flow and in which the pump is not running. Running periodically can help conserve power (e.g., battery power, electrical power, etc.) and/or can be appropriate for patients with lower risks of developing edema and/or for patients who tend to be more at risk of developing edema at certain times (e.g., during the day instead of at night, when exercising, etc.) instead of having a more constant risk. In at least some embodiments, the pump can be configured to be selectively switched between a continuous mode in which the pump runs continuously and a periodic mode in which the pump runs periodically, which can help the pump be most effectively used according to each patient's current needs.

In an exemplary embodiment, in use, the pump can include an inflow port coupled to an inflow tube in fluid communication with a lymphatic vessel of the patient, and can include an outflow port coupled to an outflow tube in fluid communication with a vein of the patient (e.g., the patient's subclavian vein, internal jugular vein, innominate vein (also referred to as a "brachiocephalic vein"), or superior vena cava). The pump can thus be configured to pump fluid from the lymphatic vessel to the vein so as to facilitate removal of fluid from the lymphatic vessel and thereby facilitate higher lymphatic return by lowering outflow pressure at the lymphatic vessel. Because lymphatic systems can have different anatomies in different patients, the inflow tube can be positioned to be in fluid communication with the patient's lymphatic duct, the patient's thoracic duct, or any duct that drains into the patient's subclavian vein, jugular vein, innominate vein, or superior vena cava.

Figure 2:
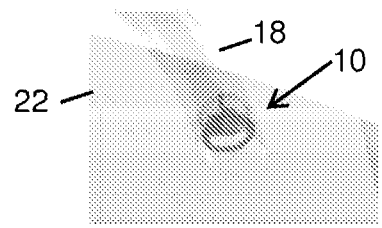
FIG. 2 is a perspective view of the implanted pump of FIG. 1.

FIGS. 1 and 2 illustrate one embodiment of a pump 10 configured to be implanted in a body of a patient. The pump 10 can have a variety of sizes, shapes, and configurations. In an exemplary embodiment, the pump 10 can include any one of a pulsatile pump, a periodical pump, and a continuous flow pump.

The pump 10 can have a size configured to facilitate implantation of the pump 10 within the patient's lung. In at least some embodiments, the pump 10 can have a size configured to allow the pump 10 to be implanted within a vein of the patient. In at least some embodiments, the pump 10 can have a size too large to be implanted with the patient's vein and small enough to be implanted within a duct of the patient, e.g., a thoracic duct of the patient or a lymphatic duct of the patient. In an exemplary embodiment, the pump 10 can have a length in a range of about 2 to 3 cm and a diameter of about 20 mm.

The pump 10 can be configured to pump fluid at a rate that facilitates draining of fluid (e.g., lymph) from the patient's lymphatic vessel. In an exemplary embodiment, the pump 10 can be configured to pump fluid at a rate in a range of about 10 to 1000 ml/hour, e.g., in a range or about 10 to 200 ml/hour, about 10 ml/hour, about 60 ml/hour, up to about 200 ml/hour, etc. In at least some embodiments, the pump 10 can have a static, e.g., unchangeable, flow rate. The flow rate can thus be predictable and/or chosen for a specific patient. In other embodiments, the pump 10 can have an adjustable flow rate. The flow rate being adjustable can help the pump 10 accommodate changes in the patient's condition over time. The flow rate can be adjustable in a variety of ways, as will be appreciated by a person skilled in the art, such as by being wirelessly adjusted using a user-operated control device located external to the patient and configured to wirelessly communicate with the pump 10 to adjust the flow rate thereof.

The pump 10 can include an inflow port configured to be coupled to an inflow tube (not shown), and can include an outflow port configured to be coupled to an outflow tube (not shown). The inflow and outflow tubes can each be removably coupled to their respective ports of the pump 10 or can each be permanently coupled to their respective ports. The inflow and outflow tubes can each be flexible to facilitate their positioning within tortuous and/or curved lumens in the patient's body. The inflow and flexible tubes can each include, e.g., indwelling catheters. In an exemplary embodiment, both of the inflow and outflow tubes are coupled to the pump 10 in a same manner, e.g., both removable or both permanent. As will be appreciated by a person skilled in the art, fluid can be configured to flow in to the pump 10 through the inflow port and out of the pump 10 through the outflow port, thereby facilitating pumping of the fluid.

Figure 3:
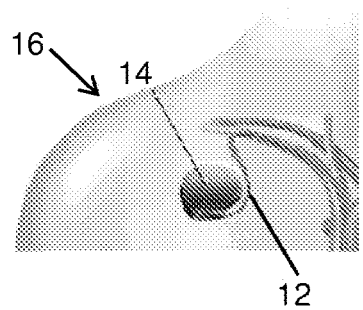
FIG. 3 is a perspective view of an implantable power source implanted in the body of FIG. 1 and in electronic communication with the pump of FIG. 1.

The pump 10 can be powered in a variety of ways. In at least some embodiments, the pump 10 can be configured to be powered by an implantable power source. In this illustrated embodiment, the pump 10 is coupled to a power lead 12, also shown in FIG. 3, coupled to an implantable power source 14. The implantable power source 14 can have a variety of sizes, shapes, and configurations. In this illustrated embodiment, the power source 14 includes a single power source in the form of a battery, but the power source can have other forms and/or can include a plurality of power sources. The power source 14 can be included as part of the pump 10. Alternatively, as in this illustrated embodiment, the power source 14 can be a separate component from the pump 10 and can be configured to be in electronic communication therewith along a power line, e.g., the power lead 12, etc. The power source 14 being a separate component from the pump 10 can allow the power source 14 to be implanted at an anatomical location outside the patient's lung, which can allow the power source 14 to have a size and/or construction that may otherwise be difficult to accommodate within a lung, and/or can facilitate replacement of the power source 14 (e.g., when the power source is depleted or is near depletion). In this illustrated embodiment, the power source 14 is implanted in a shoulder 16 of the patient, but the power source 14 can be implanted in other anatomical areas, as will be appreciated by a person skilled in the art.

Instead of the power source 14 being implanted, in at least some embodiments, the pump 10 can be configured to be powered by a power source located external to the patient. The externally-located power source can allow for a more powerful and/or larger power source than implanted power sources, and/or can help reduce an amount of material implanted into the patient, which can help reduce chances of complications. The pump 10 can be configured to wirelessly communicate with the externally-located power source to receive power therefrom. In at least some embodiments, the pump 10 can include a charging coil configured to inductively couple to the externally-located power source so as to receive power therefrom. In at least some embodiments, a handheld device can include the externally-located power source and can configured to be moved in proximity of the pump 10 to wirelessly communicate therewith. In at least some embodiments, the externally-located power source can be included as part of a wearable element that the patient can wear, e.g., on a belt, on a necklace, etc., to keep the power source in effective range of the pump 10.

The pump 10 can be configured to continuously pump fluid, e.g., continuously pump fluid through the inflow port and out the outflow port. The pump 10 can thus be configured to continuously pump fluid out of the area at which an input opening of the inflow tube coupled to the inflow port is located, e.g., out of a lymphatic vessel of the patient such as the patient's thoracic duct or lymphatic duct, and into the area at which an output opening of the outflow tube coupled to the inflow port is located, e.g., into a vein of the patient such as the patient's subclavian vein, internal jugular vein, innominate vein, or superior vena cava.

The pump 10 can be configured to periodically pump fluid, e.g., have alternating periods of pumping and no pumping. The pump 10 can be configured to periodically pump on a set schedule, e.g., alternately pump for "X" minutes and not pump for "Y" minutes, where "X" and "Y" can be equal or different. The set schedule can be preprogrammed into the pump 10, e.g., in a controller thereof (discussed further below). The set schedule can be static or can be adjustable. The set schedule can be adjustable in a variety of ways, as will be appreciated by a person skilled in the art, such as by being wirelessly adjusted using a user-operated control device located external to the patient and configured to wirelessly communicate with the pump 10 to adjust the pumping schedule thereof. Having a set schedule can allow the pump 10 to be relatively simple electronically and not require much processing capability.

Instead of having a set pumping schedule, the pump 10 can be configured to not pump (e.g., be in an idle state) until the occurrence of a trigger event. In other words, the pump 10 can have a default idle state and can be configured to move between the default idle state and an active state in which the pump 10 pumps fluid in response to the trigger event. The trigger event can be manually controlled (e.g., user-controlled) or can be dynamically controlled (e.g., non-user-controlled). A manually controlled trigger event can include a user input to the pump 10 requesting pumping. The pump 10 can thus be configured for on-demand pumping. The user can therefore cause pumping when desired (e.g., during a shortness of breath episode, when the user notices a slight weight gain, etc.) which can help the pump 10 run efficiently and when most needed as determined by the user. The user can include the patient or another person, such as the patient's doctor, the patient's caretaker, etc. The input can be provided to the pump 10 in a variety of ways. In an exemplary embodiment, the input can be provided wirelessly to the pump 10 using a user-operated control device located external to the patient and configured to wirelessly communicate with the pump 10 to cause the pump 10 to start pumping (e.g., change the pump 10 from the idle state to the active state) or to stop pumping (e.g., change the pump 10 from the active state to the idle state).

In addition or in alternative to the pump 10 being configured to pump/not pump in response to a manual trigger event, the pump 10 can be configured to dynamically switch between pumping and not pumping in response to a dynamic trigger event. A dynamic trigger event can include a value of a measured parameter being out of range as compared to a threshold value and/or threshold range of values. The parameter can be measured using a sensor (not shown) associated with the patient having the pump 10 implanted therein. Examples of sensors that can be used to measure a parameter include pressure sensors (e.g., central venous pressure (CVP) or other fluid pressure sensors, and blood pressure sensors), radio frequency transmitters and receivers, fluid sensors, bioimpedance sensors, heart rate sensors, breathing sensors, activity sensors, optical sensors. Pressure sensors can be placed, for example, in the patient's venous system, in the patient's heart, in the patient's arterial system, and/or in the patient's body at target anatomical sites that may suffer from an increase of interstitial fluid overload. Fluid sensors can be placed, for example, in the lungs. Examples of the measured parameter include pressure (e.g., as measured by a pressure sensor), fluid amount (e.g., as measured by a fluid sensor), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump 10, implanted in the patient as a separate component from the pump 10 (e.g., implanted in an interstitial space around the lung, implanted at a junction of 20 of a right subclavian vein 22 of the patient and an internal jugular vein 24 of the patient, implanted at a junction (not shown) of a left subclavian vein (not shown) of the patient and the internal jugular vein 24, etc.), or the sensor can be located external to the patient, such as by being on a skin surface thereof. If not already a part of the pump 10 so as to be in electronic communication therewith, the sensor can be configured to be in electronic communication with the pump 10 over a communication line such as a wired line or a wireless line. The sensor can include one or more sensors. In embodiments including a plurality of sensors, each of the sensors can be configured to measure the same parameter as or a different parameter than any one or more of the other sensors.

In at least some embodiments, the pump 10 can be configured to change its pumping rate (e.g., from zero to a non-zero value, from a non-zero value to zero, or from one non-zero value to another non-zero value) based on pressure measured by a pressure sensor. If the measured pressure exceeds a predetermined threshold maximum pressure value, the pump 10 can be configured to increase its pump rate (e.g., increase from zero or increase from some non-zero value) in an effort to decrease the pressure.

In at least some embodiments, the pump 10 can be configured to change its pumping rate (e.g., from zero to a non-zero value, from a non-zero value to zero, or from one non-zero value to another non-zero value) based on a fluid amount measured by a fluid sensor. If the measured fluid amount exceeds a predetermined threshold maximum fluid amount value, the pump 10 can be configured to increase its pump rate (e.g., increase from zero or increase from some non-zero value) in an effort to decrease the amount of fluid present.

In at least some embodiments, a fluid sack 11 can be implanted within the patient to facilitate continuous pumping of the pump 10. The fluid in the sack can be in fluid communication with the inflow and outflow ports of the pump 10. The fluid in the sack can include a biocompatible fluid such as saline and can include a coagulation medication. The biocompatible fluid can generally serve as a carrier for the coagulation medication. The coagulation medication can facilitate long term patency of the pump 10 by allowing circulation through the system when more robust pumping by the pump 10 is not required. The pump 10 can thus be configured to continuously pump at different rates, with the different rates being changed in response to trigger events such as those discussed above with respect to periodic pumping.

The pump 10 can include only a continuous mode of operation such that the pump 10 can only continuously pump fluid, the pump 10 can include only a periodic mode of operation such that the pump 10 can only periodically pump fluid, or the pump 10 can include the continuous and periodic modes of operation and be configured to be selectively switched between the continuous mode of operation and the periodic mode of operation. The mode switching can be accomplished in a variety of ways, as will be appreciated by a person skilled in the art such as by being wirelessly switched using a user-operated control device located external to the patient and configured to wirelessly communicate with the pump 10 to change the mode of operation thereof.

A controller (e.g., a processor, a microcontroller, etc.) in electronic communication with the pump 10 can be configured to facilitate control of the pump 10, e.g., control changing the pump's mode of operation, etc. The controller can be included as part of the pump 10 so as to be configured to be implanted in the patient with the pump 10, or, as in this illustrated embodiment, the controller can be a separate component from the pump 10. The controller being part of the pump 10 can help allow the pump 10 to be a self-contained system, although in such a controller requires space in the pump 10, which can increase a size of the pump 10. The controller being a separate component from the pump 10 can help the pump 10 have a smaller size and/or can allow the pump 10 to be controlled by a more powerful processor since the processor can be more easily upgraded than if implanted with the pump 10 and/or since the processor's size can be less important when outside the pump 10 as opposed to inside the pump 10.

Figure 4:
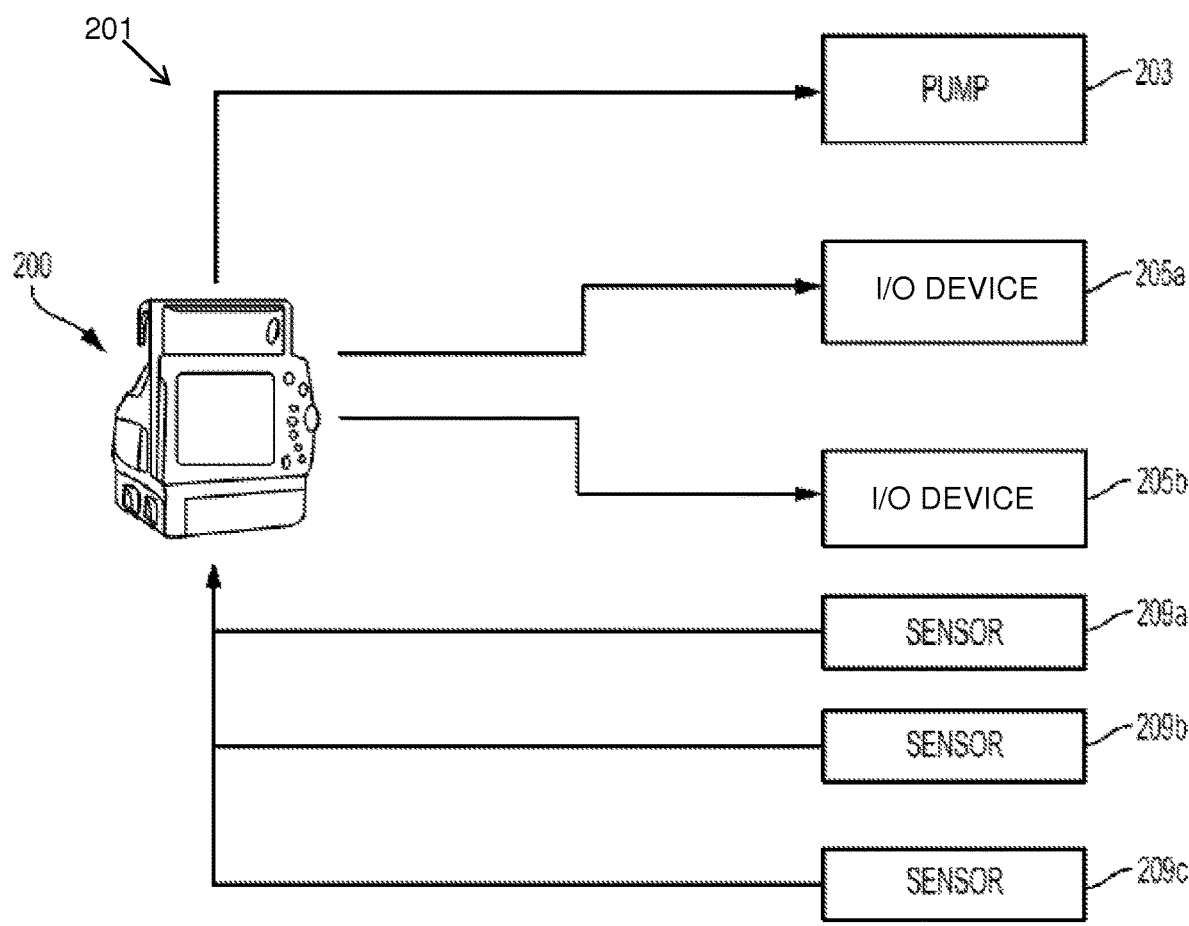
FIG. 4 is a schematic view of an embodiment of a control system for a pump configured to facilitate treatment of edema.

FIG. 4 illustrates an embodiment of a control system 200 configured to facilitate control of a pump 203, e.g., the pump 10 of FIG. 1 or any other pump disclosed herein, implanted in a patient. In general, the control system 200 can include a controller (not shown) configured to control the operation of an edema treatment system 201. The controller can include any type of microprocessor or central processing unit (CPU), including programmable general-purpose or special-purpose microprocessors and/or any one of a variety of proprietary or commercially available single or multi-processor systems. The control system 200 can also include any of a variety of additional components, such as a memory configured to can provide temporary storage and/or non-volatile storage; a bus system; a network interface configured to enable the control system 200 to communicate with other devices, e.g., other control systems, over a network; and an input/output (I/O) interface configured to connect the control system 200 with other electronic equipment such as I/O devices 205a, 205b (e.g., a keyboard, a mouse, a touchscreen, a monitor, etc.) configured to receive an input from a user. The control system 200 can be configured to electronically communicate with sensors 209a, 209b, 209c that can, as discussed herein, be used to help control the operation of the pump 203.

Referring again to the embodiment of FIGS. 1 and 2, the pump 10 is shown implanted in a right lymphatic duct 18 of the patient. The pump 10 can, however, be implanted in a variety of other anatomical locations, such as in a left lymphatic duct (not shown; also referred to as a "thoracic duct") of the patient. For reference, FIG. 1 also illustrates a right innominate vein 26 of the patient. The pump 10 can be implanted in a subcutaneous pocket created for the pump 10, which can help ensure that the pump 10 has adequate space within the patient's body.

In an exemplary embodiment, the pump 10 can be implanted adjacent the junction 20 of the right subclavian vein 22 of the patient and the internal jugular vein 24 of the patient (as in this illustrated embodiment) or adjacent the junction (not shown) of the left subclavian vein of the patient and the internal jugular vein 24. The junction 20 of the right subclavian vein 22 and the internal jugular vein 24 and the junction of the left subclavian vein and the internal jugular vein 24 are where the patient's thoracic and lymphatic ducts drain. For patients at risk of developing edema, outflow pressure at the junction 20 of the right subclavian vein 22 and the internal jugular vein 24 and at the junction of the left subclavian vein and the internal jugular vein 24 are typically highly elevated, e.g., to values greater than about 10 mmHg, over normal outflow pressure, e.g., about 5 mmHg. Pressures in excess of about 25 mmHg can completely stop lymphatic return, and during chronic elevations of pressure, lymphatic flow can be much greater than 25 mmHg. Providing the pump 10 adjacent one of these junctions can thus help regulate fluid thereat, thereby helping to prevent edema from occurring. The pump 10 can be configured to regulate the pressure at the junction to which it is adjacent to a safe, non-edemic level such as its normal level, e.g., about 5 mmHg, or within a range of about 2 to 6 mmHg. With the pump 10 located in the left or right lymphatic duct adjacent one of the junctions, the pressure regulation can be performed from within the body's natural fluid flow system, thereby allowing the pump 10 to pump at a relatively low flow rate to achieve the normal pressure level, e.g., a flow rate in a range or about 10 to 200 ml/hour, about 10 ml/hour, about 60 ml/hour, up to about 200 ml/hour, etc. This relatively low flow rate corresponds to a relatively low pressure increase on the fluid discharged into the patient's venous circulation from the outflow tube in fluid communication with the pump's output port. The pressure gradient that that pump 10 discharges against is less than about 15 mmHg. This relatively low flow rate and this pressure gradient can allow the pump 10 to function with a very low energy consumption (e.g., with a low drain on the power source 14), can allow for a very small power source (e.g., a very small battery such as those used with pacemakers and implantable cardioverter-defibrillators (ICDs)), and/or can allow for the pump 10 to be very small and thereby facilitate implantation thereof.

Figure 5:
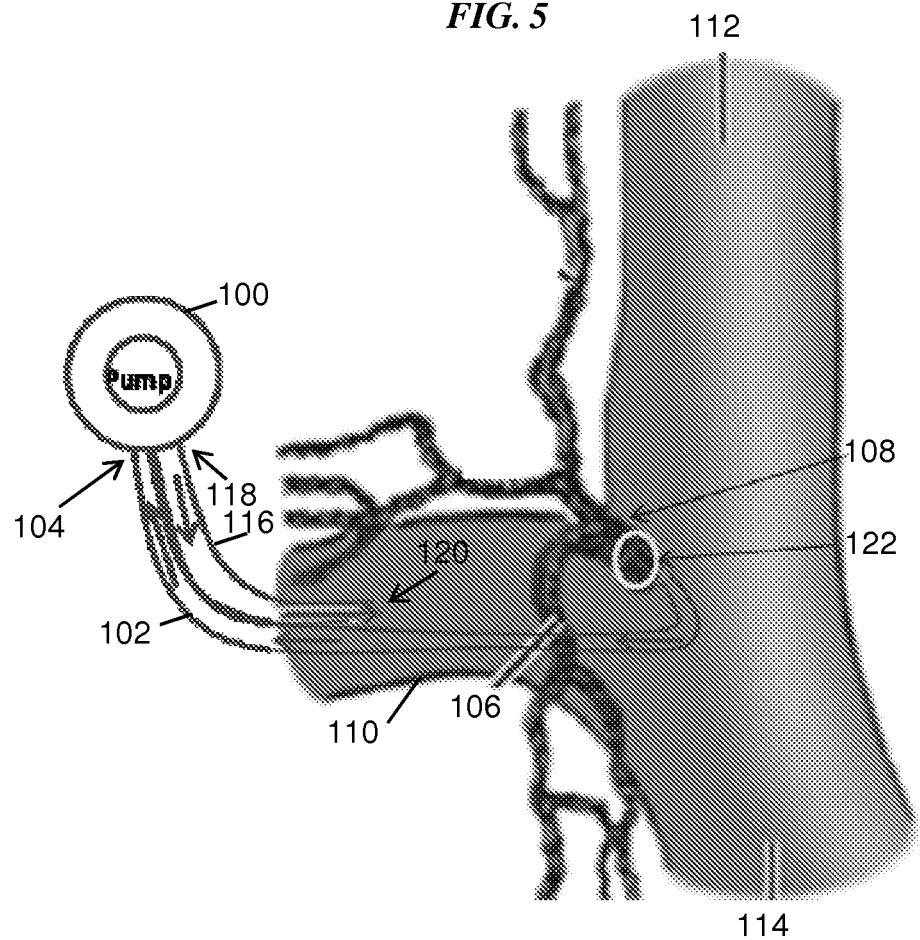
FIG. 5 is a perspective view of another embodiment of an implantable pump implanted in a body.

FIG. 5 illustrates another embodiment of a pump 100 configured to be implanted in a body of a patient. The pump 100 can generally be configured and used similar to the pump 10 of FIGS. 1 and 2. In this illustrated embodiment, the pump 100 is shown implanted in a patient. An inflow tube 102 coupled to an inflow port 104 of the pump 100 is in fluid communication with a right lymphatic duct 106 of the patient by having an inflow opening 108 thereof positioned to receive fluid therefrom, e.g., by being positioned within the right lymphatic duct 106. The inflow tube 102 extends from the right lymphatic duct 106 and through the patient's subclavian vein 110 to the pump 100. For reference, FIG. 5 also shows the patient's internal jugular vein 112 and right innominate vein 114. An outflow tube 116 coupled to an outflow port 118 of the pump 100 is in fluid communication with the subclavian vein 110 by having an outflow opening 120 thereof positioned to release fluid from the outflow tube 116 into the subclavian vein 110, e.g., by being positioned within the subclavian vein 110. FIG. 5 also indicates an area 122 of low pressure zone created by the pump 100, e.g., by pumping fluid out of the lymphatic duct 106, at the lymphatic duct 106.

Figure 6:
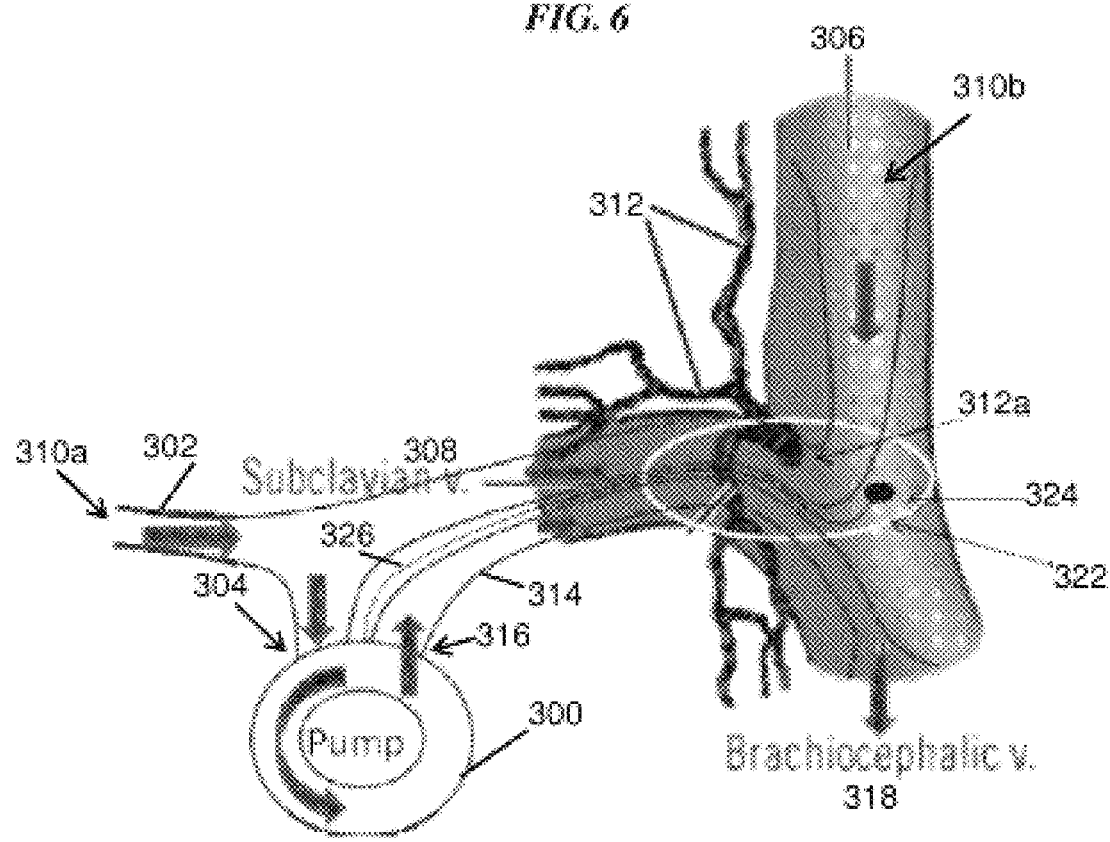
FIG. 6 is a perspective view of yet another embodiment of an implantable pump implanted in a body.

FIG. 6 illustrates yet another embodiment of a pump 300 configured to be implanted in a body of a patient. The pump 300 can generally be configured and used similar to the pump 10 of FIGS. 1 and 2. In this illustrated embodiment, the pump 300 is shown implanted in a lung of a patient. An inflow tube 302 coupled to an inflow port 304 of the pump 300 is in fluid communication with an internal jugular vein 306 of the patient and a right subclavian vein 308 of the patient by having an inflow openings 310a, 301b thereof positioned to receive fluid therefrom. For reference, FIG. 6 also shows the patient's right lymphatic duct 312 and location 312a of the lymphatic duct's outflow. An outflow tube 314 coupled to an outflow port 316 of the pump 300 is in fluid communication with a brachiocephalic vein 318 of the patient by having an outflow opening 320 thereof positioned to release fluid from the outflow tube 314 into the brachiocephalic vein 318. FIG. 6 also indicates an area 322 of low pressure zone created by the pump 300.

FIG. 6 also illustrates an embodiment of a sensor 324, a pressure sensor in this illustrated embodiment, configured to be implanted in the body of the patient. The sensor 324 can be configured to electronically communicate with the pump 300 via a communication line 326, which includes a wire in this illustrated embodiment. In this illustrated embodiment, the sensor 324 is implanted outside the inflow and outflow tubes 302, 314 and adjacent the location 312a of the right lymphatic duct's outflow at a junction of the right subclavian vein 308 and the jugular vein 306. The sensor 324 can thus be configured to sense pressure at the junction, and the pump 300 can be configured to pump in response to the pressure sensed by the sensor 324 as discussed herein.

The embodiment of FIG. 6 can be effective to treat chronic pulmonary edema and can be effective to treat acute pulmonary edema. Various embodiments of systems and methods of treating acute pulmonary edema are described in U.S. application Ser. No. 14/625,930 entitled "System And Method For Treating Pulmonary Edema" filed Feb. 19, 2015, which is hereby incorporated by reference in its entirety.

Figure 7:
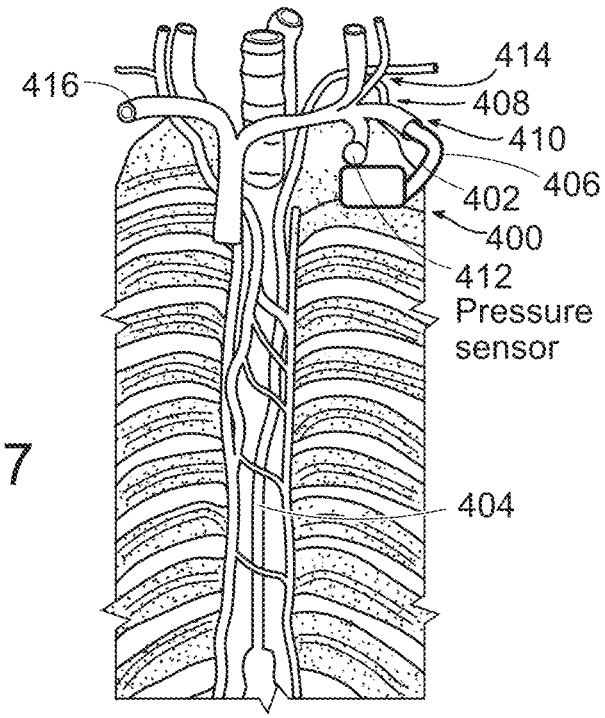
FIG. 7 is a perspective view of another embodiment of an implantable pump implanted in a body.

FIG. 7 illustrates still another embodiment of a pump 400 configured to be implanted in a body of a patient. The pump 400 can generally be configured and used similar to the pump 10 of FIGS. 1 and 2. In this illustrated embodiment, the pump 400 is shown implanted in a lung of a patient. An inflow tube 402 coupled to an inflow port (not shown) of the pump 400 is in fluid communication with an thoracic duct 404 of the patient by having an inflow opening 414 thereof positioned to receive fluid therefrom. An outflow tube 406 coupled to an outflow port (not shown) of the pump 400 is in fluid communication with a left subclavian vein 408 of the patient by having an outflow opening 410 thereof positioned to release fluid from the outflow tube 406 into the left subclavian vein 408. For reference, FIG. 7 also illustrates a right lymphatic duct 416 of the patient.

FIG. 7 also illustrates an embodiment of a sensor 412, a pressure sensor in this illustrated embodiment, configured to be implanted in the body of the patient. The sensor 412 can be configured to electronically communicate with the pump 400 via a communication line. In this illustrated embodiment, the sensor 412 is implanted outside the inflow and outflow tubes 402, 406 and in an interstitial space of the patient's lung. The sensor 412 can thus be configured to sense pressure in the lung cavity, and the pump 400 can be configured to pump in response to the pressure sensed by the sensor 412 as discussed herein.

Figure 8:
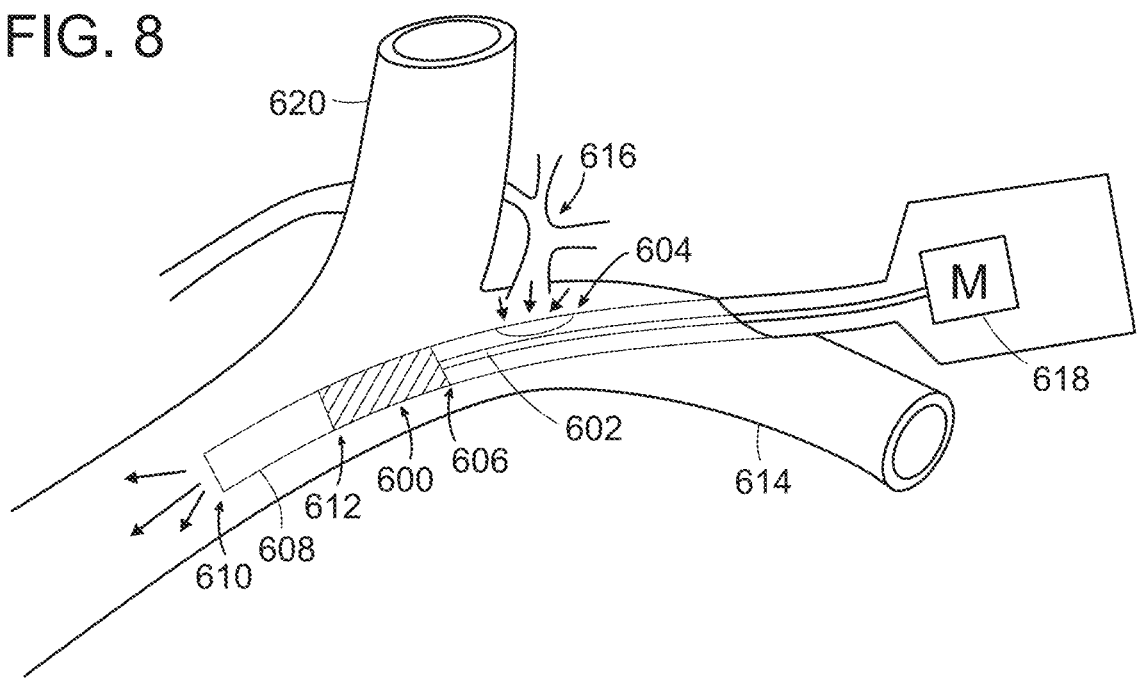
FIG. 8 is a perspective view of still another embodiment of an implantable pump implanted in a body.

FIG. 8 illustrates still another embodiment of a pump 600 configured to be implanted in a body of a patient. The pump 600 can generally be configured and used similar to the pump 10 of FIGS. 1 and 2. In this illustrated embodiment, the pump 600 is shown implanted in a lung of a patient. As illustrated, an inflow tube 602 having an inflow opening 604 can be coupled to an inflow port 606 of the pump 600, and an outflow tube 608 having an outflow opening 610 can be coupled to an outflow port 612 of the pump 600. For reference, FIG. 8 also shows the patient's left subclavian vein 614 and thoracic duct 616. The pump 600 in this illustrated embodiment is implanted at a location where the thoracic duct 616 connects with the left subclavian vein 614, but the pump 600 can be implanted elsewhere, as discussed herein.

As illustrated, the pump 600 can include an impeller, which is a type of rotor pump. In an exemplary embodiment, the pump 600 can have a diameter in a range of about 1 to 5 mm, which can facilitate its implantation within a small body space as discussed above, and can be configured to pump fluid at a rate in a range of about 10 to 100 ml/min. The pump 600 can include therein a power source (not shown) such as a battery, a controller (not shown) such as a microprocessor or other miniature control electrical board, and a motor 618 configured to drive the pump 600. The pump 600 can be configured to be activated manually for on-demand pumping and/or to be activated automatically in response to a dynamic trigger, as discussed above.

The pump 600 can be used in a variety of methods for treating pulmonary edema, as discussed further below. In general, the pump 600 can be implanted in the patient via a mini thoracotomy (similar to a pacemaker implantation procedure or ICD implantation procedure) and advanced to the location where the thoracic duct 616 connects with the left subclavian or jugular veins 614, 620. The motor 618 that drives the pump 600 can be implanted in a subcutaneous pocket located below a shoulder bone, similar to pacemaker devices. Before the implantation of the pump 600, the thoracic duct 616 can be located using a guide wire insertion via the subclavian or jugular veins. Once inside, the pump 600 can be advanced to the venous angle, and the guide wire (not shown) can be manipulated until the thoracic duct 616 is found and entered. Once the thoracic duct 616 is found, the guide wire can be kept in place inside the thoracic duct, and the pump 600 can be advanced to the location where the inflow tube 602 is in the vein 614 with the inflow opening 604 thereof as close as possible to the thoracic duct 616. Once the pump 600 is activated (manually or automatically), blood can be sucked therein and advanced to the brachiocephalic vein. Around the inflow opening 604 of the pump 600 a low pressure zone will be created, thereby allowing for the lymphatic fluids to flow more easily and thus reduce the edema.

Figure 9:
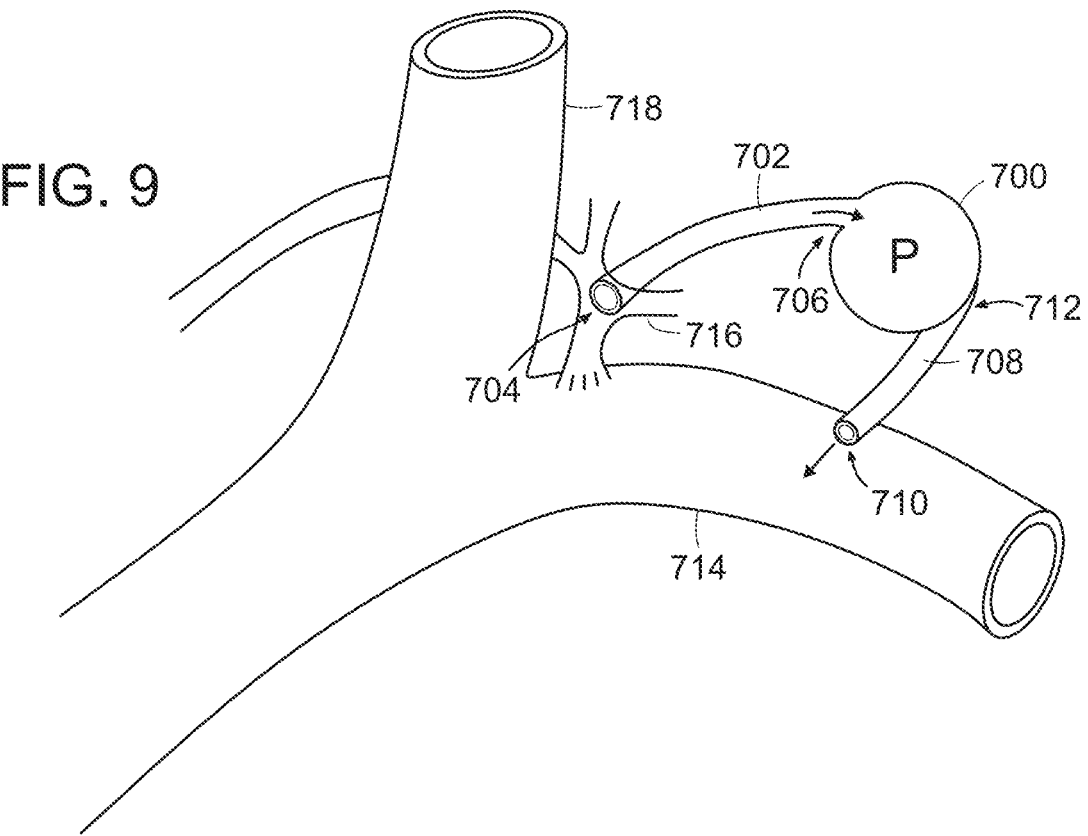
FIG. 9 is a perspective view yet still another embodiment of an implantable pump implanted in a body.

FIG. 9 illustrates yet another embodiment of a pump 700 configured to be implanted in a body of a patient. The pump 700 can generally be configured and used similar to the pump 10 of FIGS. 1 and 2. As illustrated, an inflow tube 702 having an inflow opening 704 can be coupled to an inflow port 706 of the pump 700, and an outflow tube 708 having an outflow opening 710 can be coupled to an outflow port 712 of the pump 700. For reference, FIG. 9 also shows the patient's left subclavian vein 714, thoracic duct 716, and jugular vein 718. The pump 700 in this illustrated embodiment generally provides a bypass from the thoracic duct 716 to the left subclavian vein 714, thereby allowing for a constant draining option for the lymphatic duct in case venous pressures elevate. The pump 700 can thus be configured to be automatically activated to drain fluid on demand in response to a measured increase in pressure. A bypass can be similarly provided by positioning the outflow opening 710 at the jugular vein 718 instead of the left subclavian vein 714.

Figure 10:
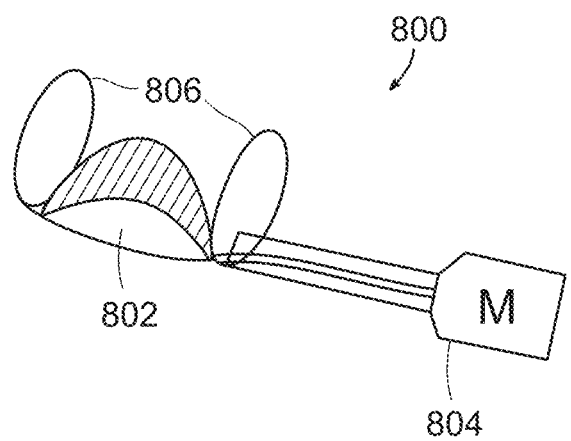
FIG. 10 is a perspective view of an embodiment of an implantable restrictor.

FIG. 10 illustrates an embodiment of an implantable restrictor 800 configured to be implanted in a body of a patient. The restrictor 800 can be configured to restrict fluid flow to facilitate draining of fluid (e.g., lymph) from the patient's lymphatic vessel, similar to the pumps described herein. The restrictor 800 can generally have a size similar to the pumps described herein, and can be configured to be implanted in a patient's body at locations described herein for the pumps.

Figure 11:
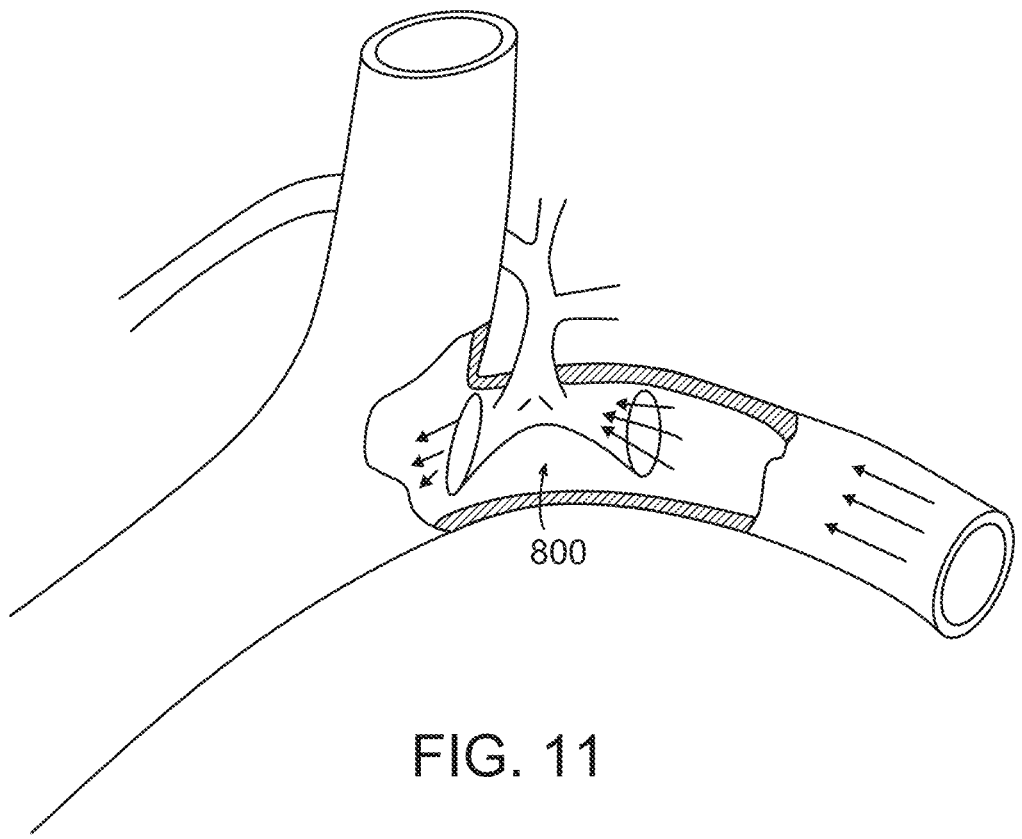
FIG. 11 is a perspective view of the restrictor of FIG. 10 implanted in a body and in an activated configuration.
Figure 12:
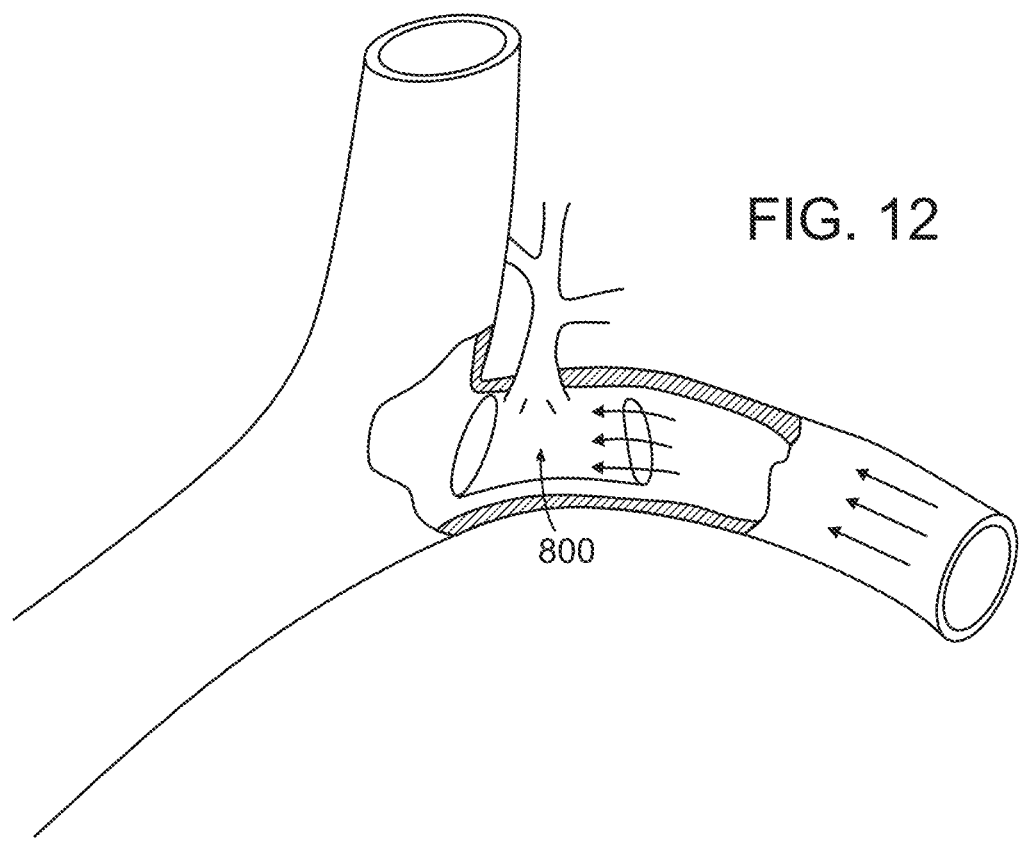
FIG. 12 is a perspective view of the restrictor of FIG. 11 implanted in the body and in a relaxed configuration.

As illustrated, the restrictor 800 can include a balloon 802 configured to move between an activated configuration, shown in FIG. 11, in which the balloon 802 is inflated and a motor 804 coupled to the restrictor 800 is activated to cause the inflation, and a relaxed configuration, shown in FIG. 12, in which the balloon is deflated and the motor 804 is not activated to allow the balloon 802 to assume its default, deflated configuration. In the activated configuration, the restrictor 800 can restrict fluid flow above the balloon 802 and consequently increase fluid flow velocity, e.g., induce the Venturi effect. The restrictor 800 is shown fully deflated in FIG. 11 and fully relaxed in FIG. 12. The balloon 802 can have any number of partially deflated configurations between the fully deflated and fully relaxed configurations. The restrictor 800 can include anchors 806 on either end of the balloon 802 to help secure the balloon 802 in position within the patient's body. In this illustrated embodiment, the restrictor 800 is implanted just above the patient's venous angle, where the thoracic duct 808 is located, thereby allowing pressure to be reduced around the venous angle. The restrictor 800 can be similarly implanted on a right side of a patient.

Figure 13:
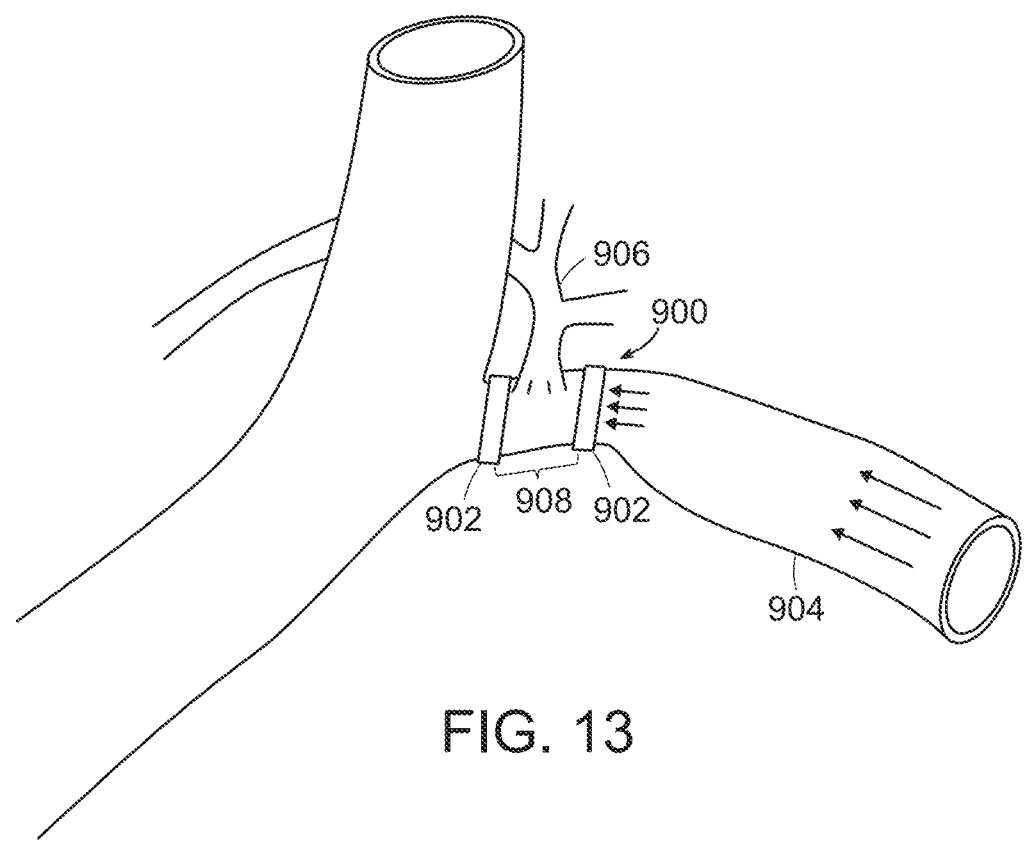
FIG. 13 is a perspective view of another embodiment of an implantable restrictor.

FIG. 13 illustrates another embodiment of an implantable restrictor 900 configured to be implanted in a body of a patient. The restrictor 900 can generally be configured and used similar to the restrictor 800 of FIGS. 10-12. The restrictor 900 can include a pair of external clips 902 configured to clip to an exterior of the subclavian or jugular vein adjacent the lymphatic or thoracic duct. The restrictor 900 can be configured to constantly restrict fluid flow through a fluid pathway 908 defined at its terminal ends by the clips 902. In other words, the restrictor 900 can be configured to provide a permanent low pressure zone (until and if the restrictor 900 is removed from the patient's body). In this illustrated embodiment, the restrictor 900 is attached to an exterior of the patient's left subclavian vein 904 adjacent the patient's thoracic duct 906.

Figure 14:
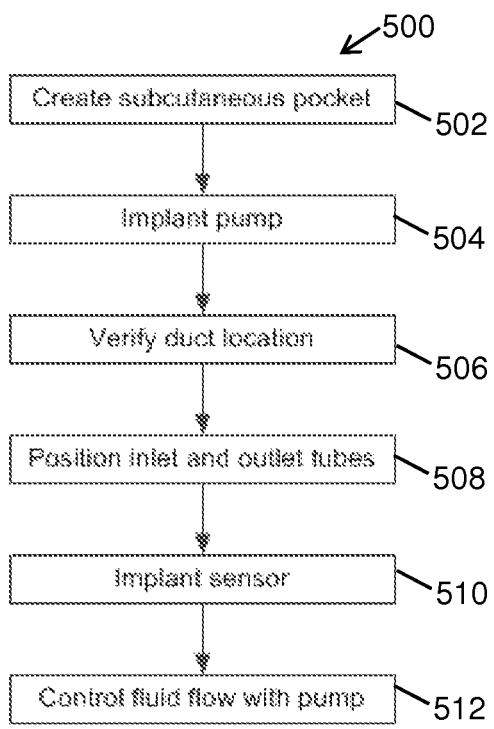
FIG. 14 is a flowchart of one embodiment of a method of treating pulmonary edema using an implanted pump.

The pumps described herein can be used in a variety of methods for treating pulmonary edema. FIG. 14 illustrates one embodiment of a method 500 for treating pulmonary edema that can be performed using a pump disclosed herein, e.g., the pump 10 of FIG. 1, the pump 100 of FIG. 5, the pump 300 of FIG. 6, the pump 400 of FIG. 7, etc.

The method 500 can include creating 502 a subcutaneous pocket in a patient to contain an implantable pump therein. The subcutaneous pocket need not be created if the patient already has a location therein that can safely accommodate the pump. The pump can be implanted 504 in the patient, either in the created subcutaneous pocket or elsewhere.

The method 500 can include verifying 506 a location of the patient's thoracic duct and/or the patient's lymphatic duct, which can help a surgeon and/or other medical professional involved in performing a surgical procedure that includes implanting 504 the pump verify that the pump, an inflow tube coupled to the pump, and/or an outflow tube coupled to the pump are implanted in the correct location within the patient. If any one or more of the pump, the inflow tube, and the outflow tube is being implanted 504 in one of the patient's thoracic duct and/or the patient's lymphatic duct, the location at least that one of the thoracic duct and lymphatic duct can be verified 506 to help ensure that the pump, the inflow tube, and/or the outflow tube are implanted 504 at the desired location.

The verification 506 can be performed in any of a variety of ways, as will be appreciated by a person skilled in the art, such as by using an imaging technique such as echo or fluoroscopy. In an exemplary embodiment, the verification 506 can include advancing a set of pig tailed wires into the patient's subclavian or jugular veins and advanced toward a junction of the jugular and subclavian veins. Once one of the pig tailed wires enters the lymphatic duct or the thoracic duct, that one of the pig tailed wires can open itself inside the duct it entered, e.g., due to a default expanded configuration of the wire. The pig tailed wires can include, for example, a default expanded circle size of 4 cm. The location of the entered duct can be verified using an imaging technique that visualizes the expanded wire therein.

FIG. 14 shows the verification 506 occurring after the implantation 504 of the pump such that the implanted location of the pump can be determined in view of the verification 506 and adjusted if need be in view of the verification 506. Additionally or alternatively, the verification 506 can be performed prior to the implantation of the pump. Similarly, the verification 506 can be performed prior to and/or after the inflow and outflow tubes are positioned 508 in the patient such that their respective inflow and outflow openings are desirably positioned, and the verification 506 can be performed prior to and/or after a sensor is implanted 510 in the patient such that their respective inflow and outflow openings are desirably positioned. As discussed above, the sensor in some embodiments is not implanted and is instead located outside the patient's body, and/or at least one sensor is implanted 510 and at least one sensor is located outside the patient's body. The inflow and outflow tubes can be positioned 508 in a variety of ways, as will be appreciated by a person skilled in the art, such as by using a central line procedure. Positioning tubes such as catheters is further described in previously mentioned U.S. application Ser. No. 14/625,930 entitled "System And Method For Treating Pulmonary Edema" filed Feb. 19, 2015.

Although not shown in FIG. 14, the method 500 can in at least some embodiments include implantation of a fluid sack either with the implantation 504 of the pump when the fluid sack is a part thereof or as a separate implantation if the fluid sack is a separate component from the pump.

Figure 15:
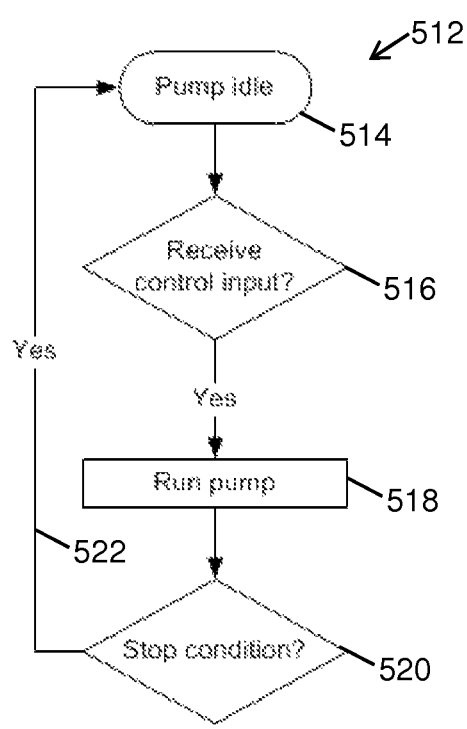
FIG. 15 is a flowchart of one embodiment of a method of controlling fluid flow using the pump in the method of FIG. 14.

With the pump implanted 504, the inflow and outflow tubes positioned 508, and, if being used in the system, the sensor implanted 510 and/or the fluid sack implanted, fluid flow can be controlled 512 with the pump. The control 512 can generally occur as described above. In at least some embodiments, controlling 512 the pump can include continuously running the pump. In at least some embodiments, controlling 512 the pump can include periodically running the pump. FIG. 15 illustrates one embodiment of controlling 512 the pump to periodically run. The pump can default to an idle state 514 in which the pump is not pumping fluid. In response to receipt 516 of a user input requesting pumping, e.g., input by a user to an I/O device in electronic communication with the pump via a control system, input wirelessly to the pump, etc., the pump can be actuated so as to run 518 and pump fluid. The pump can continue pumping until occurrence of a stop condition 520. Examples of the stop condition include a predetermined amount of time passing after the pump starts running 518 and a second user input being received that requests pumping to stop. In response to the stop condition 520 occurring, the pump can be actuated to return 522 to its idle state 514.

Figure 16:
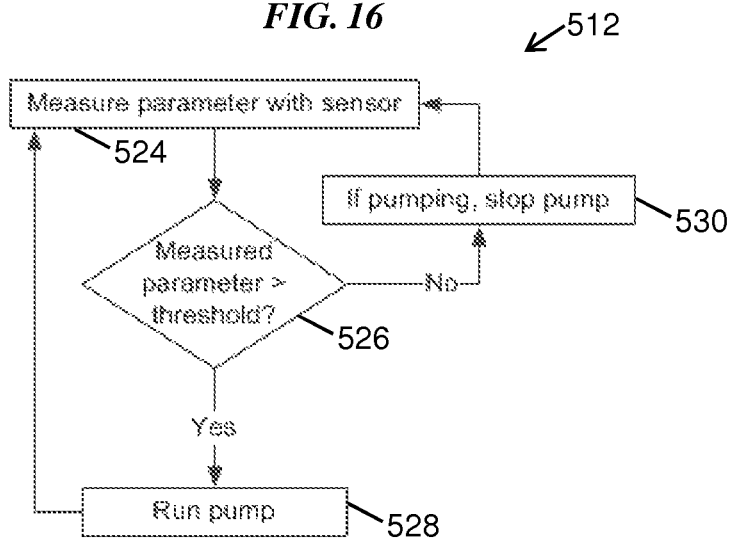
FIG. 16 is a flowchart of another embodiment of a method of controlling fluid flow using the pump in the method of FIG. 14.

FIG. 16 illustrates another embodiment of controlling 512 the pump to periodically run. A parameter can be measured 524 with a sensor (either the implanted 510 sensor or an externally-located sensor), and the pump can be actuated 528 to run in response to a value of the measured parameter being determined 526 (e.g., by a controller executing an algorithm) to be greater than a predetermined threshold value. The parameter can continue being measured 524 with the sensor, thereby allowing the pump to continue running until the measured parameter is determined 526 to be less than the predetermined threshold value. In response to the parameter being determined 526 to be less than the predetermined threshold value, the pump can be stopped 530, if it is running, and the parameter can continue being sensed to either keep the pump off or turn it back on 528.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for treating edema, the system comprising:
a pump comprising an inlet and an outlet;
an inflow tube operably coupled to the inlet;
a pressure sensor coupled to the inflow tube, wherein the inflow tube and pressure sensor are configured to be positioned in, and measure pressure in, an area of a junction of a subclavian vein and an internal jugular vein with at least a portion of the inflow tube positioned in the vicinity of a lymphatic duct outlet within the junction;
a controller operably coupled to the pressure sensor and the pump and configured to receive a pressure measurement from the pressure sensor, wherein the controller includes programming that operates the system to regulate pressure in the vicinity of the lymphatic duct outlet to a safe and normal level within a range of about 2 to 6 mmHg and that does not inhibit lymphatic return by, when the pressure measurement received from the pressure sensor indicates a pressure of at least 6 mm Hg at the junction of the subclavian vein and the internal jugular vein, triggering activation of the pump to decrease pressure in vicinity of the lymphatic duct outlet; and
a fluid sack configured to be implanted within the patient to facilitate pumping of the pump; and a fluid in the fluid sack, wherein the fluid includes a coagulation medication that facilitates long term patency of the pump.

2. The system of claim 1, wherein the controller is configured to control a speed of operation of the pump depending on a pressure measured by the pressure sensor.

3. The system of claim 1, wherein the pump is configured to continuously pump the fluid from the lymphatic duct to the vein when the pressure measured by the pressure sensor is above 6 mm Hg.

4. The system of claim 1, further comprising a power source configured to be implanted in the body of the patient and configured to provide power to the pump.

5. The system of claim 1, further comprising a charging coil configured to inductively couple to a power source external to the body of the patient and thereby provide power to the pump.

6. The system of claim 1, further comprising an indwelling catheter comprising the inflow tube.

7. The system of claim 6, wherein pressure sensor is disposed on the catheter and configured to be positioned within a venous angle at the outlet of the lymphatic duct.

8. The system of claim 6, wherein the catheter comprises a port into the inflow tube.

9. The system of claim 1, further comprising an outflow tube configured and dimensioned to be inserted through the venous angle and outflow into a subclavian vein.

10. The system of claim 9, wherein the inflow tube, the pump, and the outflow tube provide a bypass from the thoracic duct to the subclavian vein.

11. The system of claim 6, wherein the pump comprises an impeller.

12. The system of claim 11, wherein the pump has a diameter with a range of about 1 mm to 5 mm.

13. The system of claim 11, further comprising a restrictor on the catheter, the restrictor configurable to restrict fluid flow.

14. The system of claim 13, wherein the restrictor comprises a balloon configured to move between an activated configuration in which the balloon is inflated and a relaxed configuration in which the balloon is deflated.

15. The system of claim 1, wherein the pump is powered by a power source located external to the patient.

16. The system of claim 15, wherein the power source is part of a wearable element that the patient can wear.

17. The system of claim 16, wherein the wearable element is a belt or necklace.

* * * * *